United States Patent
Choy et al.

(10) Patent No.: US 10,919,864 B2
(45) Date of Patent: Feb. 16, 2021

(54) 5-FLUORO-4-IMINO-3(ALKYL/SUBSTITUTED ALKYL)-1-(ARYLSULFONYL)-3,4-DIHYDROPYRIMIDIN-2(1H)-ONE AND PROCESSES FOR THEIR PREPARATION

(71) Applicant: Adama Makhteshim Ltd., Beer Sheva (IL)

(72) Inventors: Nakyen Choy, Carmel, IN (US); Ronald Ross, Jr., Zionsville, IN (US)

(73) Assignee: Adama Makhteshim Ltd., Beer Sheva (IL)

( * ) Notice: Subject to any disclaimer, the term of this patent is extended or adjusted under 35 U.S.C. 154(b) by 0 days.

(21) Appl. No.: 16/741,026

(22) Filed: Jan. 13, 2020

(65) Prior Publication Data

US 2020/0148649 A1    May 14, 2020

Related U.S. Application Data

(63) Continuation of application No. 16/585,239, filed on Sep. 27, 2019, now abandoned, which is a continuation of application No. 16/448,633, filed on Jun. 21, 2019, now abandoned, which is a continuation of application No. 15/813,562, filed on Nov. 15, 2017, now abandoned, which is a continuation of application No. 15/173,493, filed on Jun. 3, 2016, now Pat. No. 9,850,215, which is a continuation of application No. 14/584,347, filed on Dec. 29, 2014, now abandoned.

(60) Provisional application No. 61/922,572, filed on Dec. 31, 2013, provisional application No. 61/922,582, filed on Dec. 31, 2013.

(51) Int. Cl.
C07D 239/47      (2006.01)
A61K 31/513      (2006.01)
A01N 43/54       (2006.01)

(52) U.S. Cl.
CPC .......... C07D 239/47 (2013.01); A01N 43/54 (2013.01)

(58) Field of Classification Search
CPC ..... C07D 239/47; A61K 31/513; A01N 43/54
See application file for complete search history.

(56) References Cited

U.S. PATENT DOCUMENTS

| | | |
|---|---|---|
| 3,309,359 A | 3/1967 | Duschinsky et al. |
| 3,368,938 A | 2/1968 | Berger et al. |
| 3,635,977 A | 1/1972 | Lutz et al. |
| 3,868,373 A | 2/1975 | Hoffer |
| 4,009,272 A | 2/1977 | Konig et al. |
| 4,845,081 A | 7/1989 | Sloan |
| 4,996,208 A | 2/1991 | Lindner et al. |
| 5,962,489 A | 10/1999 | Mueller et al. |
| 6,066,638 A | 5/2000 | Bereznak et al. |
| 6,617,330 B2 | 9/2003 | Walter |
| 7,914,799 B2 | 3/2011 | Jira et al. |
| 8,263,603 B2 | 9/2012 | Boebel et al. |
| 8,318,758 B2 | 11/2012 | Boebel et al. |
| 8,470,839 B2 | 6/2013 | Boebel et al. |
| 8,552,020 B2 | 10/2013 | Pobanz et al. |
| 8,658,660 B2 | 2/2014 | Boebel et al. |
| 8,916,579 B2 | 12/2014 | Boebel et al. |
| 9,000,002 B2 | 4/2015 | Pobanz et al. |
| 9,006,259 B2 | 4/2015 | Webster et al. |
| 9,271,497 B2 | 3/2016 | Lorsbach et al. |
| 9,321,734 B2 | 4/2016 | Lorsbach et al. |
| 9,526,245 B2 | 12/2016 | Owen et al. |
| 9,532,570 B2 | 1/2017 | Owen et al. |
| 9,538,753 B2 | 1/2017 | Owen et al. |
| 9,622,474 B2 | 4/2017 | Lorsbach et al. |
| 9,642,368 B2 | 5/2017 | Lorsbach et al. |
| 9,840,475 B2 | 12/2017 | Lorsbach et al. |
| 9,840,476 B2 | 12/2017 | Choy et al. |
| 9,850,215 B2 | 12/2017 | Choy et al. |
| 9,862,686 B2 | 1/2018 | Boebel et al. |
| 9,908,855 B2 | 3/2018 | Lorsbach et al. |
| 10,045,533 B2 | 8/2018 | Owen et al. |
| 10,045,534 B2 | 8/2018 | Owen et al. |

(Continued)

FOREIGN PATENT DOCUMENTS

| | | |
|---|---|---|
| EP | 0102908 | 3/1984 |
| EP | 0139613 | 5/1985 |

(Continued)

OTHER PUBLICATIONS

Feb. 8, 2018 Non-Final Office Action issued by the U.S. Patent and Trademark Office in connection with U.S. Appl. No. 15/813,562.

(Continued)

*Primary Examiner* — Bruck Kifle

(74) *Attorney, Agent, or Firm* — Gary J. Gershik

(57) ABSTRACT

Provided herein are 5-fluoro-4-imino-3-(alkyl/substituted alkyl)-1-(arylsulfonyl)-3,4-dihydropyrimidin-2(1H)-one and processes for their preparation which may include the use of an alkali carbonate and an alkylating agent

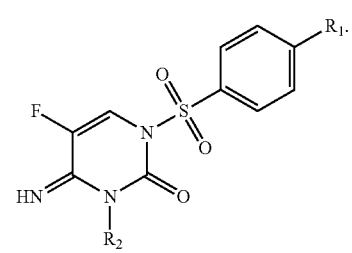

20 Claims, No Drawings

(56) References Cited

U.S. PATENT DOCUMENTS

| | | |
|---|---|---|
| 10,051,862 B2 | 8/2018 | Owen et al. |
| 10,059,703 B2 | 8/2018 | Lorsbach et al. |
| 2003/0039667 A1 | 2/2003 | Jira et al. |
| 2008/0004253 A1 | 1/2008 | Bra Nstetter et al. |
| 2008/0269238 A1 | 10/2008 | Sugihara et al. |
| 2009/0203647 A1 | 8/2009 | Benko et al. |
| 2010/0022538 A1 | 1/2010 | Boebel et al. |
| 2010/0029482 A1 | 2/2010 | Benko et al. |
| 2010/0029483 A1 | 2/2010 | Iskandar et al. |
| 2011/0034490 A1 | 2/2011 | Boebel et al. |
| 2011/0034491 A1 | 2/2011 | Boebel et al. |
| 2011/0034492 A1 | 2/2011 | Boebel et al. |
| 2011/0034493 A1 | 2/2011 | Boebel et al. |
| 2011/0053891 A1 | 3/2011 | Boebel et al. |
| 2011/0082162 A1 | 4/2011 | Lorsbach et al. |
| 2011/0263627 A1 | 10/2011 | Boebel et al. |
| 2013/0045984 A1 | 2/2013 | Boebel et al. |
| 2014/0011824 A1 | 1/2014 | Pobanz et al. |
| 2015/0111851 A1 | 4/2015 | Boebel et al. |
| 2015/0181874 A1 | 7/2015 | Owen et al. |
| 2015/0181875 A1 | 7/2015 | Owen et al. |
| 2015/0181883 A1 | 7/2015 | Owen et al. |
| 2015/0183749 A1 | 7/2015 | Choy et al. |
| 2015/0183750 A1 | 7/2015 | Choy et al. |
| 2015/0191436 A1 | 7/2015 | Webster et al. |
| 2015/0342188 A1 | 12/2015 | Lorsbach et al. |
| 2015/0353506 A1 | 12/2015 | Lorsbach et al. |
| 2015/0359225 A1 | 12/2015 | Lorsbach et al. |
| 2016/0192653 A1 | 7/2016 | Lorsbach et al. |
| 2016/0198711 A1 | 7/2016 | Lorsbach et al. |
| 2016/0280662 A1 | 9/2016 | Choy et al. |
| 2016/0280663 A1 | 9/2016 | Choy et al. |
| 2017/0008855 A1 | 1/2017 | Boebel et al. |
| 2017/0086458 A1 | 3/2017 | Owen et al. |
| 2017/0086459 A1 | 3/2017 | Owen et al. |
| 2017/0086460 A1 | 3/2017 | Owen et al. |
| 2017/0204069 A1 | 7/2017 | Lorsbach et al. |
| 2017/0240540 A1 | 8/2017 | Lorsbach et al. |
| 2018/0000082 A1 | 1/2018 | Klittich et al. |
| 2018/0072686 A1 | 3/2018 | Choy et al. |
| 2018/0303094 A1 | 10/2018 | Owen et al. |
| 2018/0303095 A1 | 10/2018 | Owen et al. |
| 2018/0303096 A1 | 10/2018 | Owen et al. |
| 2019/0308941 A1 | 10/2019 | Choy et al. |
| 2019/0373891 A1 | 12/2019 | Owen et al. |
| 2019/0380342 A1 | 12/2019 | Owen et al. |
| 2019/0380343 A1 | 12/2019 | Owen et al. |
| 2020/0024238 A1 | 1/2020 | Choy et al. |
| 2020/0100500 A1 | 4/2020 | Owen et al. |
| 2020/0113182 A1 | 4/2020 | Owen et al. |
| 2020/0113183 A1 | 4/2020 | Owen et al. |
| 2020/0221698 A1 | 7/2020 | Owen et al. |
| 2020/0229438 A1 | 7/2020 | Owen et al. |
| 2020/0245623 A1 | 8/2020 | Owen et al. |

FOREIGN PATENT DOCUMENTS

| | | |
|---|---|---|
| EP | 0332579 | 9/1989 |
| EP | 0877022 | 4/2003 |
| EP | 1952689 | 8/2008 |
| GB | 1461184 | 1/1997 |
| JP | 6001793 | 1/1994 |
| JP | 2002-530409 | 9/2002 |
| JP | 2012-502905 | 2/2012 |
| JP | 2013-501728 | 1/2013 |
| NZ | 597644 | 9/2014 |
| WO | WO 97/33890 A1 | 9/1997 |
| WO | WO 02/30922 A2 | 4/2002 |
| WO | WO 2008/083465 A1 | 7/2008 |
| WO | WO 2009/094442 A2 | 7/2009 |
| WO | WO 2010/047866 A2 | 4/2010 |
| WO | WO 2010/085377 A2 | 7/2010 |
| WO | WO 2011/017538 A1 | 2/2011 |
| WO | WO 2011/017540 A1 | 2/2011 |
| WO | WO 2011/017544 A1 | 2/2011 |
| WO | WO 2011/017545 A1 | 2/2011 |
| WO | WO 2011/017547 A1 | 2/2011 |
| WO | WO 2011/043876 A1 | 4/2011 |
| WO | WO 2011/137002 A1 | 11/2011 |
| WO | WO 2013/025795 A1 | 2/2013 |
| WO | WO 2014/105821 A1 | 7/2014 |
| WO | WO 2014/105841 A1 | 7/2014 |
| WO | WO 2014/105844 A1 | 7/2014 |
| WO | WO 2014/105845 A1 | 7/2014 |
| WO | WO 2015/103142 A1 | 7/2015 |
| WO | WO 2015/103144 A1 | 7/2015 |
| WO | WO 2015/103259 A1 | 7/2015 |
| WO | WO 2015/103261 A1 | 7/2015 |
| WO | WO 2015/103262 A1 | 7/2015 |
| WO | WO 2016/106138 A1 | 6/2016 |

OTHER PUBLICATIONS

May 8, 2018 Response to Feb. 8, 2018 Non-Final Office Action issued by the U.S. Patent and Trademark Office in connection with U.S. Appl. No. 15/813,562.

Jun. 8, 2018 Final Office Action issued by the U.S. Patent and Trademark Office in connection with U.S. Appl. No. 15/813,562.

Oct. 19, 2018 Response to Jun. 8, 2018 Final Office Action issued by the U.S. Patent and Trademark Office in connection with U.S. Appl. No. 15/813,562.

Oct. 24, 2018 Advisory Action issued by the U.S. Patent and Trademark Office in connection with U.S. Appl. No. 15/813,562.

Nov. 15, 2018 Final Office Action issued by the U.S. Patent and Trademark Office in connection with U.S. Appl. No. 15/813,562.

Nov. 20, 2018 Communication vacating Nov. 15, 2018 Final Office Action issued by the U.S. Patent and Trademark Office in connection with U.S. Appl. No. 15/813,562.

Feb. 21, 2019 Final Office Action issued by the U.S. Patent and Trademark Office in connection with U.S. Appl. No. 15/813,562.

Apr. 17, 2019 Response to Feb. 21, 2019 Final Office Action issued by the U.S. Patent and Trademark Office in connection with U.S. Appl. No. 15/813,562.

Apr. 24, 2019 Advisory Action issued by the U.S. Patent and Trademark Office in connection with U.S. Appl. No. 15/813,562.

Jan. 23, 2019 Non-Final Office Action issued by the U.S. Patent and Trademark Office in connection with U.S. Appl. No. 16/021,977.

Apr. 23, 2019 Response Jan. 23, 2019 Non-Final Office Action issued by the U.S. Patent and Trademark Office in connection with U.S. Appl. No. 16/021,977.

Jan. 23, 2019 Non-Final Office Action issued by the U.S. Patent and Trademark Office in connection with U.S. Appl. No. 16/022,007.

Apr. 23, 2019 Response to Jan. 23, 2019 Non-Final Office Action issued by the U.S. Patent and Trademark Office in connection with U.S. Appl. No. 16/022,007.

Jan. 23, 2019 Non-Final Office Action issued by the U.S. Patent and Trademark Office in connection with U.S. Appl. No. 16/022,027.

Apr. 23, 2019 Response to Jan. 23, 2019 Non-Final Office Action issued by the U.S. Patent and Trademark Office in connection with U.S. Appl. No. 16/022,027.

Mar. 8, 2019 Response to Office Action issued by the Argentinean Patent Office in connection with Argentinean Patent Application No. 20110101423.

Report Previous to Final Decision issued by the Argentinean Patent Office in connection with Argentinean Patent Application No. 20110101423 (including English language translation).

Dec. 17, 2019 Response to Report Previous to Final Decision issued by the Argentinean Patent Office in connection with Argentinean Patent Application No. 20110101423.

May 3, 2018 Final Technical Report issued by the Costa Rican Patent Office in connection with Costa Rican Patent Application No. 2012-0584.

Oct. 30, 2018 Appeal filed in response to Aug. 14, 2018 Decision of Rejection issued by the Costa Rican Patent Office in connection with Costa Rican Patent Application No. 2012-0584.

Jun. 4, 2019 Technical Report issued by the Costa Rican Patent Office in connection with Costa Rican Patent Application No. 2012-0584.

(56) References Cited

OTHER PUBLICATIONS

May 30, 2018 Response to Mar. 27, 2018 Office Action issued by the Indian Patent Office in connection with Indian Patent Application No. 10041/DELNP/2012.
Jun. 22, 2018 Hearing Notice for Aug. 23, 2018 Hearing issued by the Indian Patent Office in connection with Indian Patent Application No. 10041/DELNP/2012.
Sep. 6, 2018 Response to Aug. 23, 2018 Hearing conducted by the Indian Patent Office in connection with Indian Patent Application No. 10041/DELNP/2012.
Feb. 15, 2019 Office Action issued by the Filipino Patent Office in connection with Filipino Patent Application No. 1/2012/502138.
Apr. 15, 2019 Response to Feb. 15, 2019 Office Action issued by the Filipino Patent Office in connection with Filipino Patent Application No. 1/2012/502138.
May 22, 2018 Communication pursuant to Article 94(3) issued by the European Patent Office in connection with European Patent Application No. 14877285.8.
Sep. 21, 2018 Response to May 22, 2018 Communication pursuant to Article 94(3) issued by the European Patent Office in connection with European Patent Application No. 14877285.8.
Nov. 19, 2018 Communication pursuant to Article 94(3) issued by the European Patent Office in connection with European Patent Application No. 14877285.8.
May 29, 2019 Response to Nov. 19, 2018 Communication pursuant to Article 94(3) issued by the European Patent Office in connection with European Patent Application No. 14877285.8.
Nov. 4, 2019 Summons to attend Oral Proceedings pursuant to Rule 115(1) EPC issued by the European Patent Office in connection with European Patent Application No. 14877285.8.
Apr. 17, 2020 Written Submissions to Nov. 4, 2019 Summons to attend Oral Proceedings pursuant to Rule 115(1) EPC issued by the European Patent Office in connection with European Patent Application No. 14877285.8.
Jul. 11, 2018 Office Action issued by the Eurasian Patent Office in connection with Eurasian Patent Application No. 201691353 (including English language translation).
Jun. 7, 2019 Office Action issued by the Aripo Patent Office in connection with ARIPO Application No. AP/P/20 I 61009342.
Dec. 4, 2019 Response to Jun. 7, 2019 Office Action issued by the ARIPO Patent Office in connection with ARIPO Application No. AP/P/20 I 61009342.
Jul. 23, 2019 Office Action issued by the Brazilian Patent Office in connection with Brazilian Patent Application No. BR 102014033010-0 (including English language translation).
Oct. 18, 2019 Response to Jul. 23, 2019 Office Action issued by the Brazilian Patent Office in connection with Brazilian Patent Application No. BR 102014033010-0.
Apr. 3, 2020 Office Action issued by the Brazilian Patent Office in connection with Brazilian Patent Application No. BR 102014033010-0.
Jan. 16, 2019 Office Action issued by the Belizean Patent Office in connection with Belize Patent Application No. 881.16.
Apr. 4, 2018 Office Action issued by the Chinese Patent Office in connection with Chinese Patent Application No. 201480076563.7 (including English language translation).
Aug. 20, 2018 Response to Apr. 4, 2018 Office Action issued by the Chinese Patent Office in connection with Chinese Patent Application No. 201480076563.7.
Nov. 16, 2018 Office Action issued by the Chinese Patent Office in connection with Chinese Patent Application No. 201480076563.7 (including English language translation).
Mar. 1, 2019 Response to Nov. 16, 2018 Office Action issued by the Chinese Patent Office in connection with Chinese Patent Application No. 201480076563.7.
Mar. 22, 2019 Office Action issued by the Chinese Patent Office in connection with Chinese Patent Application No. 201480076563.7 (including English language translation).

Jun. 6, 2019 Response to Mar. 22, 2019 Office Action issued by the Chinese Patent Office in connection with Chinese Patent Application No. 201480076563.7.
Aug. 27, 2019 Decision of Final Rejection issued by the Chinese Patent Office in connection with Chinese Patent Application No. 201480076563.7 (including English language translation).
Jun. 18, 2019 Office Action issued by the Colombian Patent Office in connection with Colombian Patent Application No. NC2016-0000512.
Oct. 29, 2019 Response to Jun. 18, 2019 Office Action issued by the Colombian Patent Office in connection with Colombian Patent Application No. NC2016-0000512.
Dec. 13, 2018 Office Action issued by the Dominican Republic Patent Office in connection with Dominican Patent Application No. P2016-0163 (including English language translation).
Apr. 24, 2019 Response to Dec. 13, 2018 Office Action issued by the Dominican Republic Patent Office in connection with Dominican Patent Application No. P2016-0163.
May 13, 2019 Office Action issued by the Dominican Republic Patent Office in connection with Dominican Patent Application No. P2016-0163 (including English language translation).
Aug. 28, 2019 Response to May 13, 2019 Office Action issued by the Dominican Republic Patent Office in connection with Dominican Patent Application No. P2016-0163.
Feb. 10, 2020 Office Action issued by the Dominican Republic Patent Office in connection with Dominican Patent Application No. P2016-0163 (including English language translation).
Nov. 18, 2018 Response to Jul. 18, 2018 Office Action issued by the Israeli Patent Office in connection with Israeli Patent Application No. 246511.
Dec. 30, 2018 Office Action issued by the Israeli Patent Office in connection with Israeli Patent Application No. 246511.
Jun. 30, 2019 Response to Dec. 30, 2018 Office Action issued by the Israeli Patent Office in connection with Israeli Patent Application No. 246511.
May 13, 2019 First Examination Report issued by the Indian Patent Office in connection with Indian Patent Application No. 201617025518.
Oct. 23, 2019 Response to May 13, 2019 First Examination Report issued by the Indian Patent Office in connection with Indian Patent Application No. 201617025518.
Nov. 1, 2019 Hearing Notice issued for Nov. 21, 2019 Hearing by the Indian Patent Office in connection with Indian Patent Application No. 201617025518.
Dec. 5, 2019 Response to Nov. 21, 2019 Hearing with the Indian Patent Office in connection with Indian Patent Application No. 201617025518.
Feb. 28, 2019 Response to Aug. 28, 2018 Office Action issued by the Japanese Patent Office in connection with Japanese Patent Application No. 2016-543746.
Apr. 9, 2019 Office Action issued by the Japanese Patent Office in connection with Japanese Patent Application No. 2016-543746 (including English language translation).
Oct. 9, 2019 Response to Apr. 9, 2019 Office Action issued by the Japanese Patent Office in connection with Japanese Patent Application No. 2016-543746.
Jan. 21, 2020 Office Action issued by the Japanese Patent Office in connection with Japanese Patent Application No. 2016-543746 (including English language translation).
Oct. 31, 2019 Office Action issued by the Sri Lankan Patent Office in connection with Sri Lankan Patent Application No. 18863.
Jul. 9, 2018 Response to Jun. 8, 2018 Office Action issued by the Mexican Patent Office in connection with Mexican Patent Application No. MX/a/2016/008758.
Feb. 11, 2019 Response to Oct. 9, 2018 Office Action issued by the Mexican Patent Office in connection with Mexican Patent Application No. MX/a/2016/008758.
Oct. 11, 2019 Response to Jun. 11, 2019 Office Action issued by the Mexican Patent Office in connection with Mexican Patent Application No. MX/a/2016/008758.
Aug. 17, 2018 Office Action issued by the Filipino Patent Office in connection with Filipino Patent Application No. 1/2016/501284.

(56) References Cited

OTHER PUBLICATIONS

Dec. 6, 2018 Response to Aug. 17, 2018 Office Action issued by the Filipino Patent Office in connection with Filipino Patent Application No. 1/2016/501284.
Oct. 15, 2019 Office Action issued by the Filipino Patent Office in connection with Filipino Patent Application No. 1/2016/501284.
Sep. 2, 2019 Office Action issued by the Singaporean Patent Office in connection with Singaporean Patent Application No. 11201605372Q.
Dec. 17, 2019 Response to Sep. 2, 2019 Office Action issued by the Singaporean Patent Office in connection with Singaporean Patent Application No. 11201605372Q.
May 8, 2018 Response to Dec. 12, 2017 Technical Examination Report issued by the Salvadorian Patent Office in connection with Salvadorian Patent Application No. 20160020316.
Jan. 15, 2019 Technical Examination Report issued by the Salvadorian Patent Office in connection with Salvadorian Patent Application No. 20160020316 (including English language translation).
May 24, 2019 Response to Jan. 15, 2019 Technical Examination Report issued by the Salvadorian Patent Office in connection with Salvadorian Patent Application No. 20160020316.
Aug. 30, 2019 Technical Examination Report issued by the Salvadorian Patent Office in connection with Salvadorian Patent Application No. 20160020316 (including English language translation).
Oct. 31, 2018 Response to Jul. 31, 2018 Office Action issued by the Taiwanese Patent Office in connection with Taiwanese Patent Application No. 103146555.
Jan. 14, 2019 Office Action issued by the Taiwanese Patent Office in connection with Taiwanese Patent Application No. 103146555.
May 2, 2019 Response to Jan. 14, 2019 Office Action issued by the Taiwanese Patent Office in connection with Taiwanese Patent Application No. 103146555.
Aug. 12, 2019 Office Action issued by the Taiwanese Patent Office in connection with Taiwanese Patent Application No. 103146555.
Apr. 14, 2020 Response to Aug. 12, 2019 Office Action issued by the Taiwanese Patent Office in connection with Taiwanese Patent Application No. 103146555.
Jul. 17, 2019 Office Action issued by the Ukranian Patent Office in connection with Ukranian Patent Application No. a 2016 08339 (including English language translation).
Sep. 13, 2019 Response to Jul. 17, 2019 Office Action issued by the Ukranian Patent Office in connection with Ukranian Patent Application No. a 2016 08339.
May 28, 2019 Office Action issued by the Vietnamese Patent Office in connection with Vietnamese Patent Application No. 1-2016-02804 (including English language translation).
Aug. 21, 2019 Response to May 28, 2019 Office Action issued by the Vietnamese Patent Office in connection with Vietnamese Patent Application No. 1-2016-02804.
May 22, 2018 Communication pursuant to Article 94(3) EPC issued by the European Patent Office in connection with European Patent Application No. 14875976.4.
Sep. 21, 2018 Response to May 22, 2018 Communication pursuant to Article 94(3) EPC issued by the European Patent Office in connection with European Patent Application No. 14875976.4.
Nov. 19, 2018 Communication pursuant to Article 94(3) EPC issued by the European Patent Office in connection with European Patent Application No. 14875976.4.
May 29, 2019 Response to Nov. 19, 2018 Communication pursuant to Article 94(3) EPC issued by the European Patent Office in connection with European Patent Application No. 14875976.4.
Nov. 4, 2019 Summons to attend Oral Proceedings pursuant to Rule 115(1) EPC issued by the European Patent Office in connection with European Patent Application No. 14875976.4.
Apr. 17, 2020 Written Submissions to Nov. 4, 2019 Summons to attend Oral Proceedings pursuant to Rule 115(1) EPC issued by the European Patent Office in connection with European Patent Application No. 14875976.4.
May 28, 2018 Response to Jan. 26, 2018 Office Action issued by the Eurasian Patent Office in connection with Eurasian Patent Application No. 201691351.
Jul. 31, 2019 Response to Aug. 31, 2018 Office Action issued by the Eurasian Patent Office in connection with Eurasian Patent Application No. 201691351.
Oct. 25, 2019 Office Action issued by the Eurasian Patent Office in connection with Eurasian Patent Application No. 201691351 (including English language translation).
Feb. 25, 2020 Response to Oct. 25, 2019 Office Action issued by the Eurasian Patent Office in connection with Eurasian Patent Application No. 201691351.
Jul. 23, 2019 Office Action issued by the Brazilian Patent Office in connection with Brazilian Patent Application No. BR 102014033037-2 (including English language translation).
Oct. 18, 2019 Response to Jul. 23, 2019 Office Action issued by the Brazilian Patent Office in connection with Brazilian Patent Application No. BR 102014033037-2.
Apr. 15, 2020 Office Action issued by the Brazilian Patent Office in connection with Brazilian Patent Application No. BR 102014033037-2.
Apr. 4, 2018 Office Action issued by the Chinese Patent Office in connection with Chinese Patent Application No. 201480076583.4.
Aug. 20, 2018 Response to Apr. 4, 2018 Office Action issued by the Chinese Patent Office in connection with Chinese Patent Application No. 201480076583.4.
Dec. 10, 2018 Office Action issued by the Chinese Patent Office in connection with Chinese Patent Application No. 201480076583.4 (including English language translation).
Feb. 25, 2019 Response to Dec. 10, 2018 Office Action issued by the Chinese Patent Office in connection with Chinese Patent Application No. 201480076583.4.
Apr. 18, 2019 Office Action issued by the Chinese Patent Office in connection with Chinese Patent Application No. 201480076583.4 (including English language translation).
Aug. 5, 2019 Response to Apr. 18, 2019 Office Action issued by the Chinese Patent Office in connection with Chinese Patent Application No. 201480076583.4.
Jul. 17, 2018 Office Action issued by the Israeli Patent Office in connection with Israeli Patent Application No. 246512.
Nov. 7, 2018 Response to Jul. 17, 2018 Office Action issued by the Israeli Patent Office in connection with Israeli Patent Application No. 246512.
Dec. 30, 2018 Office Action issued by the Israeli Patent Office in connection with Israeli Patent Application No. 246512.
Jun. 30, 2019 Response to Dec. 30, 2018 Office Action issued by the Israeli Patent Office in connection with Israeli Patent Application No. 246512.
Apr. 26, 2019 First Examination Report issued by the Indian Patent Office in connection with Indian Patent Application No. 201617025525.
Sep. 16, 2019 Response to Apr. 26, 2019 First Examination Report issued by the Indian Patent Office in connection with Indian Patent Application No. 201617025525.
Jan. 21, 2019 Response to Aug. 21, 2018 Office Action issued by the Japanese Patent Office in connection with Japanese Patent Application No. 2016-543735.
Feb. 19, 2019 Office Action issued by the Japanese Patent Office in connection with Japanese Patent Application No. 2016-543735 (including English language translation).
Jul. 19, 2019 Response to Feb. 19, 2019 Office Action issued by the Japanese Patent Office in connection with Japanese Patent Application No. 2016-543735.
Jun. 5, 2019 Office Action issued by the Mexican Patent Office in connection with Mexican Patent Application No. MX/a/2016/008759.
Sep. 11, 2019 Response to Jun. 5, 2019 Office Action issued by the Mexican Patent Office in connection with Mexican Patent Application No. MX/a/2016/008759.
Dec. 16, 2019 Office Action issued by the Mexican Patent Office in connection with Mexican Patent Application No. MX/a/2016/008759.
Sep. 28, 2018 Response to Jul. 6, 2018 Office Action issued by the Thai Patent Office in connection with Thai Patent Application No. 1601003881.
Jun. 21, 2019 Response to Office Action issued by the Thai Patent Office in connection with Thai Patent Application No. 1601003881.

(56) References Cited

OTHER PUBLICATIONS

Sep. 19, 2018 Office Action issued by the Taiwanese Patent Office in connection with Taiwan Patent Application No. 103146560.
Dec. 17, 2018 Response to Sep. 19, 2018 Office Action issued by the Taiwanese Patent Office in connection with Taiwan Patent Application No. 103146560.
May 29, 2019 Office Action issued by the Vietnamese Patent Office in connection with Vietnamese Patent Application No. Jan. 2016-02803 (including English language translation).
Aug. 21, 2019 Response to May 29, 2019 Office Action issued by the Vietnamese Patent Office in connection with Vietnamese Patent Application No. 1-2016-02803.
Aug. 14, 2018 Decision of Rejection issued by the Costa Rican Patent Office in connection with Costa Rican Patent Application No. 2012-0584.
Aug. 28, 2018 Notice of Appeal filed in response to Aug. 14, 2018 Decision of Rejection issued by the Costa Rican Patent Office in connection with Costa Rican Patent Application No. 2012-0584.
Aug. 16, 2018 Office Action issued by the Cuban Patent Office in connection with Cuban Patent Application No. 2016-0099 (including English language translation).
Aug. 28, 2018 Office Action issued by the Japanese Patent Office in connection with Japanese Patent Application No. 2016-543746 (including English language translation).
Aug. 21, 2018 Office Action issued by the Japanese Patent Office in connection with Japanese Patent Application No. 2016-543735 (including English language translation).
Aug. 31, 2018 Office Action issued by the Eurasian Patent Office in connection with Eurasian Patent Application No. 201691351 (including English language translation).
Jul. 31, 2018 Office Action issued by the Taiwanese Patent Office in connection with Taiwan Patent Application No. 103146555.
PCT International Search Report dated Sep. 21, 2010 in connection with PCT International Application No. PCT/US2010/044579 (WO 2011/017540), filed Aug. 5, 2010.
PCT International Search Report dated Sep. 21, 2010 in connection with PCT International Application No. PCT/US2010/044592 (WO 2011/017547), filed Aug. 5, 2010.
PCT International Search Report dated Sep. 23, 2010 in connection with PCT International Application No. PCT/US2010/044576 (WO 2011/017538), filed Aug. 5, 2010.
International Search Report dated Jul. 5, 2011 in connection with PCT International Application No. PCT/US2011/033203 (WO 2011/137002), filed Apr. 20, 2011.
Written Opinion of the International Searching Authority dated Jul. 5, 2011 in connection with PCT International Application No. PCT/US2011/033203 (WO 2011/137002), filed Apr. 20, 2011.
International Preliminary Report on Patentability dated Oct. 30, 2012 in connection with PCT International Application No. PCT/US2011/033203 (WO 2011/137002), filed Apr. 20, 2011.
PCT International Search Report dated Oct. 15, 2012 in connection with PCT International Application No. PCT/US2012/050930 (WO 2013/025795), filed Aug. 15, 2012.
Written Opinion of the International Searching Authority dated Oct. 15, 2012 in connection with PCT International Application No. PCT/US2012/050930 (WO 2013/025795), filed Aug. 15, 2012.
International Preliminary Report on Patentability dated Feb. 18, 2014 in connection with PCT International Application No. PCT/US2012/050930 (WO 2013/025795), filed Aug. 15, 2012.
International Search Report dated Apr. 22, 2014 in connection with PCT International Application No. PCT/US2013/077542 (WO 2014/105845), filed Dec. 23, 2013.
Written Opinion of the International Searching Authority dated Apr. 22, 2014 in connection with PCT International Application No. PCT/US2013/077542 (WO 2014/105845), filed Dec. 23, 2013.
International Preliminary Report on Patentability dated Jun. 30, 2015 in connection with PCT International Application No. PCT/US2013/077542 (WO 2014/105845), filed Dec. 23, 2013.

International Search Report dated Apr. 8, 2015 in connection with PCT International Application No. PCT/US2014/072566 (WO 2015/103142), filed Dec. 29, 2014.
International Preliminary Report on Patentability dated Jul. 5, 2016 in connection with PCT International Application No. PCT/US2014/072566 (WO 2015/103142), filed Dec. 29, 2014.
Written Opinion of the International Searching Authority dated Apr. 8, 2015 in connection with PCT International Application No. PCT/US2014/072566 (WO 2015/103142), filed Dec. 29, 2014.
International Search Report dated Apr. 2, 2015 in connection with PCT International Application No. PCT/US2014/072569 (WO 2015/103144), filed Dec. 29, 2014.
International Preliminary Report on Patentability issued Jul. 5, 2016 in connection with PCT International Application No. PCT/US2014/072569 (WO 2015/103144), filed Dec. 29, 2014.
Written Opinion of the International Searching Authority dated Apr. 2, 2015 in connection with PCT International Application No. PCT/US2014/072569 (WO 2015/103144), filed Dec. 29, 2014.
International Search Report dated Apr. 28, 2015 in connection with PCT International Application No. PCT/US2014/072745 (WO 2015/103259), filed Dec. 30, 2014.
International Preliminary Report on Patentability dated Jul. 5, 2016 in connection with PCT International Application No. PCT/US2014/072745 (WO 2015/103259), filed Dec. 30, 2014.
Written Opinion of the International Searching Authority dated Apr. 28, 2015 in connection with PCT International Application No. PCT/US2014/072745 (WO 2015/103259), filed Dec. 30, 2014.
International Search Report dated Apr. 29, 2015 in connection with PCT International Application No. PCT/US2014/072747 (WO 2015/103261), filed Dec. 30, 2014.
International Preliminary Report on Patentability dated Jul. 5, 2016 in connection with PCT International Application No. PCT/US2014/072747 (WO 2015/103261), filed Dec. 30, 2014.
Written Opinion of the International Searching Authority dated Apr. 29, 2015 in connection with PCT International Application No. PCT/US2014/072747 (WO 2015/103261), filed Dec. 30, 2014.
International Search Report dated May 21, 2015 in connection with PCT International Application No. PCT/US2014/072748 (WO 2015/103262), filed Dec. 30, 2014.
International Preliminary Report on Patentability dated Jul. 5, 2016 in connection with PCT International Application No. PCT/US2014/072748 (WO 2015/103262), filed Dec. 30, 2014.
Written Opinion of the International Searching Authority dated May 21, 2015 in connection with PCT International Application No. PCT/US2014/072748 (WO 2015/103262), filed Dec. 30, 2014.
PCT International Search Report dated Feb. 25, 2016 in connection with PCT International Application No. PCT/US2015/066756 (WO 2016/106138), filed Dec. 18, 2015.
International Preliminary Report on Patentability dated Jun. 27, 2017 in connection with PCT International Application No. PCT/US2015/066756 (WO 2016/106138), filed Dec. 18, 2015.
Written Opinion of the International Searching Authority dated Feb. 25, 2016 in connection with PCT International Application No. PCT/US2015/066756 (WO 2016/106138), filed Dec. 18, 2015.
PCT International Search Report dated Sep. 30, 2009 in connection with PCT International Application No. PCT/US/2009/031683 (WO 2009/094442), filed Jan. 22, 2009.
PCT International Search Report dated Mar. 14, 2011 in connection with PCT International Application No. PCT/US/2011/020351 (WO 2011/085084), filed Jan. 6, 2011.
PCT International Search Report dated Oct. 1, 2010 in connection with PCT International Application No. PCT/US/2010/044588 (WO 2011/017545), filed Aug. 5, 2010.
PCT International Search Report dated Oct. 9, 2012 in connection with PCT International Application No. PCT/US/2012/050931 (WO 2013/025796), filed Aug. 15, 2012.
International Search Report dated Apr. 22, 2011 in connection with PCT International Application No. PCT/US/2010/060792 (WO 2011/084611), filed Dec. 16, 2010.
Nov. 10, 2011 Non-Final Office Action issued by the U.S. Patent and Trademark Office in connection with U.S. Appl. No. 13/090,616.

(56) References Cited

OTHER PUBLICATIONS

Feb. 9, 2012 Response to Nov. 10, 2011 Non-Final Office Action issued by the U.S. Patent and Trademark Office in connection with U.S. Appl. No. 13/090,616.
May 14, 2013 Non-Final Office Action issued by the U.S. Patent and Trademark Office in connection with U.S. Appl. No. 13/586,450.
Aug. 14, 2013 Response to May 14, 2013 Non-Final Office Action issued by the U.S. Patent and Trademark Office in connection with U.S. Appl. No. 13/586,450.
Mar. 4, 2015 Non-Final Office Action issued by the U.S. Patent and Trademark Office in connection with U.S. Appl. No. 14/584,347.
Jun. 4, 2015 Response to Mar. 4, 2015 Non-Final Office Action issued by the U.S. Patent and Trademark Office in connection with U.S. Appl. No. 14/584,347.
Jul. 2, 2015 Final Office Action issued by the U.S. Patent and Trademark Office in connection with U.S. Appl. No. 14/584,347.
Sep. 2, 2015 Response to Jul. 2, 2015 Final Office Action issued by the U.S. Patent and Trademark Office in connection with U.S. Appl. No. 14/584,347.
Sep. 9, 2015 Advisory Action issued by the U.S. Patent and Trademark Office in connection with U.S. Appl. No. 14/584,347.
Nov. 23, 2016 Office Action issued by the U.S. Patent and Trademark Office in connection with U.S. Appl. No. 15/173,493.
Mar. 1, 2017 Response to Nov. 23, 2016 Non-Final Office Action issued by the U.S. Patent and Trademark Office in connection with U.S. Appl. No. 15/173,493.
Mar. 15, 2017 Non-Final Office Action issued by the U.S. Patent and Trademark Office in connection with U.S. Appl. No. 15/173,493.
Aug. 14, 2017 Response to Mar. 15, 2017 Non-Final Office Action issued by the U.S. Patent and Trademark Office in connection with U.S. Appl. No. 15/173,493.
Mar. 5, 2015 Non-Final Office Action issued by the U.S. Patent and Trademark Office in connection with U.S. Appl. No. 14/584,368.
Jun. 4, 2015 Response to Mar. 5, 2015 Non-Final Office Action issued by the U.S. Patent and Trademark Office in connection with U.S. Appl. No. 14/584,368.
Jul. 2, 2015 Final Office Action issued by the U.S. Patent and Trademark Office in connection with U.S. Appl. No. 14/584,368.
Sep. 2, 2015 Response to Jul. 2, 2015 Final Office Action issued by the U.S. Patent and Trademark Office in connection with U.S. Appl. No. 14/584,368.
Sep. 10, 2015 Advisory Action issued by the U.S. Patent and Trademark Office in connection with U.S. Appl. No. 14/584,368.
Dec. 1, 2016 Office Action issued by the U.S. Patent and Trademark Office in connection with U.S. Appl. No. 15/173,529.
Mar. 1, 2017 Response to Dec. 1, 2016 Non-Final Office Action issued by the U.S. Patent and Trademark Office in connection with U.S. Appl. No. 15/173,529.
Mar. 20, 2017 Office Action issued by the U.S. Patent and Trademark Office in connection with U.S. Appl. No. 15/173,529.
Aug. 15, 2017 Response to Mar. 20, 2017 Office Action issued by the U.S. Patent and Trademark Office in connection with U.S. Appl. No. 15/173,529.
Dec. 18, 2015 Non-Final Office Action issued by the U.S. Patent and Trademark Office in connection with U.S. Appl. No. 14/585,945.
Mar. 16, 2016 Response to Dec. 18, 2015 Non-Final Office Action issued by the U.S. Patent and Trademark Office in connection with U.S. Appl. No. 14/585,945.
Apr. 11, 2016 Final Office Action issued by the U.S. Patent and Trademark Office in connection with U.S. Appl. No. 14/585,945.
Aug. 11, 2016 Response to Apr. 11, 2016 Final Office Action issued by the U.S. Patent and Trademark Office in connection with U.S. Appl. No. 14/585,945.
Oct. 5, 2017 Non-Final Office Action issued by the U.S. Patent and Trademark Office in connection with U.S. Appl. No. 15/377,845.
Jan. 5, 2018 Response to Oct. 5, 2017 Non-Final Office Action issued by the U.S. Patent and Trademark Office in connection with U.S. Appl. No. 15/377,845.
Jan. 26, 2018 Final Office Action issued by the U.S. Patent and Trademark Office in connection with U.S. Appl. No. 15/377,845.
Mar. 26, 2018 Response to Jan. 26, 2018 Final Office Action issued by the U.S. Patent and Trademark Office in connection with U.S. Appl. No. 15/377,845.
Dec. 18, 2015 Non-Final Office Action issued by the U.S. Patent and Trademark Office in connection with U.S. Appl. No. 14/585,952.
Mar. 16, 2016 Response to Dec. 18, 2015 Non-Final Office Action issued by the U.S. Patent and Trademark Office in connection with U.S. Appl. No. 14/585,952.
Apr. 12, 2016 Final Office Action issued by the U.S. Patent and Trademark Office in connection with U.S. Appl. No. 14/585,952.
Aug. 11, 2016 Response to Apr. 12, 2016 Final Office Action issued by the U.S. Patent and Trademark Office in connection with U.S. Appl. No. 14/585,952.
Oct. 5, 2017 Non-Final Office Action issued by the U.S. Patent and Trademark Office in connection with U.S. Appl. No. 15/377,854.
Jan. 5, 2018 Response to Oct. 5, 2017 Non-Final Office Action issued by the U.S. Patent and Trademark Office in connection with U.S. Appl. No. 15/377,854.
Jan. 26, 2018 Final Office Action issued by the U.S. Patent and Trademark Office in connection with U.S. Appl. No. 15/377,854.
Mar. 26, 2018 Response to Jan. 26, 2018 Final Office Action issued by the U.S. Patent and Trademark Office in connection with U.S. Appl. No. 15/377,854.
Dec. 18, 2015 Non-Final Office Action issued by the U.S. Patent and Trademark Office in connection with U.S. Appl. No. 14/585,962.
Mar. 16, 2016 Response to Dec. 18, 2015 Non-Final Office Action issued by the U.S. Patent and Trademark Office in connection with U.S. Appl. No. 14/585,962.
Apr. 12, 2016 Final Office Action issued by the U.S. Patent and Trademark Office in connection with U.S. Appl. No. 14/585,962.
Aug. 12, 2016 Response to Apr. 12, 2016 Final Office Action issued by the U.S. Patent and Trademark Office in connection with U.S. Appl. No. 14/585,962.
Oct. 5, 2017 Non-Final Office Action issued by the U.S. Patent and Trademark Office in connection with U.S. Appl. No. 15/377,859.
Jan. 5, 2018 Response to Oct. 5, 2017 Non-Final Office Action issued by the U.S. Patent and Trademark Office in connection with U.S. Appl. No. 15/377,859.
Jan. 25, 2018 Final Office Action issued by the U.S. Patent and Trademark Office in connection with U.S. Appl. No. 15/377,859.
Mar. 26, 2018 Response to Jan. 25, 2018 Final Office Action issued by the U.S. Patent and Trademark Office in connection with U.S. Appl. No. 15/377,859.
Abdel-Aziz et al. (2008) "Synthesis of some novel pyrazolo[1,5-a]pyrimidine, 1,2,4-triazolo[1,5-a]pyrimidine, pyrido[2,3-d]pyrimidine, pyrazolo[5,1-c]-1,2,4-triazine and 1,2,4-triazolo[5,1-c]-1,2,4-triazine derivatives incorporating a thiazolo[3,2-a]benzimidazole moiety." J. Heterocyclic Chem. 45(4):1033-1037 (Abtract only).
Bera et al. (2002) "Nucleosides with Furanyl Scaffolds." Tetrahedron, Elsevier Science Publishers. 58(24):4865-4871.
Birari et al. (2009) "Synthesis of Cytosine Derivatives and Study of their Alkylation Under Mild Conditions," Organic Preparations and Procedures International: The New Journal for Organic Synthesis, 41(6):515-532.
Chiacchio et al. (2003) "Enantioselective Syntheses and Cytotoxicity of N,O-Nucleosides." J. of Medicinal Chemistry, American Chemical Society. 46(1):3696-3702.
Duschinsky et al. (1966) "Nucleosides. XXXIII. N4-Acylated 5-Fluorocytosines and a Direct Synthesis of 5-Fluoro-2'-deoxycytidine." J. of Medicinal Chemistry. 9(4):566-572.
Duschinsky et al. (1964) "Cytosine derivatives." CAPLUS Abstract 61:18527.
Gabriella et al. (1963) "Some 5-fluorosulfanilamidopyrimidines." Gazzette Chimica Italiana. 93(10):1268-1278.
Jaworski et al. (1990) "Infrared spectra and tautomerism of 5-fluorocytosine, 5-bromocytosine and 5-iodocytosine Matrix isolation and theoretical ab initio studies." J. of Molecular Structure. 223:63-92.
Kulikowski et al. (1978) "Methylation and tautomerism of 5-fluorocytosine nucleosides and their analogues." J. Nucleic Acids Research, Special Publication. 4(1):S7-S10.

(56) References Cited

OTHER PUBLICATIONS

Lewis et al. (1995) "Synthesis and in vitro anti-human cytomegalovirus (hcmv) activity of certain alkenyl substituted cytosines and 5-halocytosines." J. of Heterocyclic Chemistry. 32(5):1513-1515.
Liang et al. (2007) "A facile synthesis and herbicidal activities of novel fluorine-containing thiazolo[4,5-d] pyrimidin-7(6H)-ones." J. of Fluorine Chemistry, 128(7):879-884.
Robins et al. (1972) "A direct synthesis of 5-fluorocytosine and its nucleosides using trifluromethyl hypofluorite." J. of the Chemical Society, Chemical Communications. 1(1):18-19.
Suzuki et al. (1968) "Studies on Pyrimidine Derivatives." Chemical and Pharmaceutical Bulletin, 16(4):750-755.
Waring (2009) "Defining optimum lipophilicity and molecular weight ranges for drug candidates-Molecular weight dependent lower logD limits based on permeability." Bioorganic & Medicinal Chemistry Letters, 19(10):2844-2851.
Woese et al. (1990) "Towards a natural system of organisms: Proposal for the domains Archaea, Bacteria, and Eucarya." Proc. Acad. Sci., 87:4576-4579.
Zhang et al. (1989) "Improved method for synthesis of 5-fluorocytosine (5-FC)." Caplus Abstract, 111:134074.
FRAC Code List: Fungicide sorted by mode of action, (Dec. 31, 2009), pp. 1-10, available at http://www.frac.info/frac/publication/anhangFRAC_Code_List_2010.pdf.
Patani & LaVoie (1996) "Bioisosterism: A Rational Approach in Drug Design." Chemical Reviews, 96(8):3147-3176.
Jul. 4, 2013 European Search Opinion & Search Report issued by the EPO in connection with European Patent Application No. 11775446.5, filed Apr. 20, 2011.
Feb. 3, 2014 Response to Jul. 4, 2013 European Search Opinion issued by the EPO in connection with European Patent Application No. 11775446.5.
Sep. 25, 2014 Communication pursuant to Article 94(3) EPC issued by the European Patent Office in connection with European Patent Application No. 11775446.5.
Feb. 4, 2015 Response to Sep. 25, 2014 Communication pursuant to Article 94(3) EPC issued by the European Patent Office in connection with European Patent Application No. 11775446.5.
Aug. 28, 2014 First Examination Report issued by the Australian Patent Office in connection with Australian Patent Application No. 2011245544.
Mar. 23, 2015 Response to Aug. 28, 2014 First Examination Report issued by the Australian Patent Office in connection with Australian Patent Application No. 2011245544.
Jan. 11, 2017 Office Action issued by the Canadian Patent Office in connection with Canadian Patent Application No. 2,797,226.
Jul. 11, 2017 Response to Jan. 11, 2017 Office Action issued by the Canadian Patent Office in connection with Canadian Patent Application No. 2,797,226.
Sep. 28, 2017 Office Action issued by the Canadian Patent Office in connection with Canadian Patent Application No. 2,797,226.
Mar. 28, 2018 Response to Sep. 28, 2017 Office Action issued by the Canadian Patent Office in connection with Canadian Patent Application No. 2,797,226.
Aug. 25, 2015 Office Action issued by the Chilean Patent Office in connection with Chilean Patent Application No. 2979-2012.
May 26, 2016 Office Action issued by the Chilean Patent Office in connection with Chilean Patent Application No. 2979-2012.
Aug. 22, 2016 Response to May 26, 2016 Office Action issued by the Chilean Patent Office in connection with Chilean Patent Application No. 2979-2012.
Oct. 17, 2013 Office Action issued by the Chinese Patent Office in connection with Chinese Patent Application No. 201180031680.8.
Feb. 28, 2014 Response to Oct. 17, 2013 Office Action issued by the Chinese Patent Office in connection with Chinese Patent Application No. 201180031680.8.
May 23, 2014 Office Action issued by the Chinese Patent Office in connection with Chinese Patent Application No. 201180031680.8.
Aug. 7, 2014 Response to May 23, 2014 Office Action issued by the Chinese Patent Office in connection with Chinese Patent Application No. 201180031680.8 (including English language translation).
Sep. 24, 2013 Office Action issued by Colombian Patent Office in connection with Colombian Patent Application No. 12213540.
Dec. 18, 2013 Response to Sep. 24, 2013 Office Action issued by Colombian Patent Office in connection with Colombian Patent Application No. 12213540.
Oct. 3, 2017 Office Action issued by the Costa Rican Patent Office in connection with Costa Rican Patent Application No. 2012-0584 (including English language translation).
Nov. 20, 2017 Response to Oct. 3, 2017 Office Action issued by the Costa Rican Patent Office in connection with Costa Rican Patent Application No. 2012-0584.
Jan. 28, 2018 Office Action issued by the Costa Rican Patent Office in connection with Costa Rican Patent Application No. 2012-0584 (including English language translation).
Mar. 6, 2018 Response to Jan. 28, 2018 Office Action issued by the Costa Rican Patent Office in connection with Costa Rican Patent Application No. 2012-0584.
Feb. 19, 2018 Response to Jan. 5, 2018 Office Action issued by the Indonesian Patent Office in connection with Indonesian Patent No. W-00 2012 004824 (including English language translation).
Jun. 22, 2015 Response to Mar. 22, 2015 Office Action issued by the Israeli Patent Office in connection with Israeli Patent Application No. 222646.
Nov. 30, 2017 Office Action issued by the Indian Patent Office in connection with Indian Patent Application No. 10041/DELNP/2012 (including English language translation).
Mar. 22, 2018 Response to Nov. 30, 2017 Office Action issued by the Indian Patent Office in connection with Indian Patent Application No. 10041/DELNP/2012 (English language translation).
Mar. 27, 2018 Office Action issued by the Indian Patent Office in connection with Indian Patent Application No. 10041/DELNP/2012 (English language translation).
Feb. 10, 2015 Office Action issued by the Japanese Patent Office in connection with Japanese Patent Application No. 2013-508042.
May 10, 2015 Response to Feb. 10, 2015 Office Action issued by the Japanese Patent Office in connection with Japanese Patent Application No. 2013-508042.
Mar. 22, 2017 Notice of Preliminary Rejection issued by Korean Patent Office in connection with Korean Patent Application No. 10-2012-7030690 (including English language translation).
May 22, 2017 Response to Mar. 22, 2017 Notice of Preliminary Rejection issued by Korean Patent Office in connection with Korean Patent Application No. 10-2012-7030690 (including English language translation).
Jul. 3, 2014 Response to May 26, 2014 Office Action issued by the Mexican Patent Office Mexican Patent Application No. MX/a/2012/012530.
Jun. 14, 2013 First Examination Report issued by the New Zealand Patent Office in connection with New Zealand Patent Application No. 603151.
Oct. 1, 2013 Response to Jun. 14, 2013 First Examination Report issued by the New Zealand Patent Office in connection with New Zealand Patent Application No. 603151.
Jun. 17, 2016 Office Action issued by the Filipino Patent Office in connection with Filipino Patent Application No. 1/2012/502138.
Sep. 28, 2016 Office Action issued by the Filipino Patent Office in connection with Filipino Patent Application No. 1/2012/502138.
Jan. 19, 2015 Office Action issued by the Russian Patent Office in connection with Russian Patent Application No. 2012150293.
Apr. 19, 2015 Response to Jan. 19, 2015 Office Action issued by the Russian Patent Office in connection with Russian Patent Application No. 2012150293.
Apr. 16, 2014 Office Action issued by the Ukrainian Patent Office in connection with Ukrainian Patent Application No. 2012 13412.
Oct. 30, 2014 Response to Apr. 16, 2014 Office Action issued by the Ukrainian Patent Office in connection with Ukrainian Patent Application No. 2012 13412.
Oct. 5, 2016 Communication pursuant to Rules 161(2) and 162 EPC issued by the European Patent Office in connection with European Patent Application No. 14877285.8.

(56) References Cited

OTHER PUBLICATIONS

Jun. 21, 2017 Communication pursuant to Rule 164(1) EPC and Partial Supplementary European Search Report issued by the European Patent Office in connection with European Patent Application No. 14877285.8.
Aug. 16, 2017 Response to Jun. 21, 2017 Communication and Partial Supplementary European Search Report pursuant to Rule 164(1) EPC issued by the European Patent Office in connection with European Patent Application No. 14877285.8.
Sep. 13, 2017 Supplementary European Search Report issued by the European Patent Office in connection with European Patent Application No. 14877285.8.
Sep. 29, 2017 Communication pursuant to Rules 70(2) and 70a(2) issued by the European Patent Office in connection with European Patent Application No. 14877285.8.
Mar. 28, 2018 Response to Sep. 13, 2017 Supplementary European Search Report issued by the European Patent Office in connection with European Patent Application No. 14877285.8.
May 15, 2017 Office Action issued by the Eurasian Patent Office in connection with Eurasian Patent Application No. 201691353 (including English language translation).
Sep. 15, 2017 Response to May 15, 2017 Office Action issued by the Eurasian Patent Office in connection with Eurasian Patent Application No. 201691353.
Dec. 22, 2017 Office Action issued by the Eurasian Patent Office in connection with Eurasian Patent Application No. 201691353 (including English language translation).
Apr. 23, 2018 Response to Dec. 22, 2017 Office Action issued by the Eurasian Patent Office in connection with Eurasian Patent Application No. 201691353 (including amended claims in English).
Dec. 23, 2016 First Examination Report issued by the Australian Patent Office in connection with Australian Patent Application No. 2014373959.
Sep. 27, 2017 Response to Dec. 23, 2016 First Examination Report issued by the Australian Patent Office in connection with Australian Patent Application No. 2014373959.
Jul. 28, 2017 First Substantive Report issued by the Chilean Patent Office in connection with Chilean Patent Application No. 2016-001677.
Oct. 26, 2017 Response to Jul. 28, 2017 First Substantive Report issued by the Chilean Patent Office in connection with Chilean Patent Application No. 2016-001677.
Dec. 19, 2017 Second Substantive Report issued by the Chilean Patent Office in connection with Chilean Patent Application No. 2016-001677.
Mar. 15, 2018 Response to Dec. 19, 2017 Second Substantive Report issued by the Chilean Patent Office in connection with Chilean Patent Application No. 2016-001677.
Aug. 9, 2016 Office Action issued by the Colombian Patent Office in connection with Colombian Patent Application No. NC2016-0000512.
Feb. 20, 2018 Office Action issued by the Colombian Patent Office in connection with Colombian Patent Application No. NC2016-0000512.
Mar. 20, 2018 Response to Feb. 20, 2018 Office Action issued by the Colombian Patent Office in connection with Colombian Patent Application No. NC2016-0000512.
Jul. 14, 2016 Office Action issued by the Cuban Patent Office in connection with Cuban Patent Application No. 2016-0099.
Oct. 6, 2016 Response to Jul. 14, 2016 Office Action issued by the Cuban Patent Office in connection with Cuban Patent Application No. 2016-0099.
Nov. 20, 2016 Response to Jul. 20, 2016 Notice Before Examination issued by the Israeli Patent Office in connection with Israeli Patent Application No. 246511.
Jan. 12, 2017 First Examination Report issued by the New Zealand Patent Office in connection with New Zealand Patent Application No. 722439.
Jul. 12, 2017 Response to Jan. 12, 2017 First Examination Report issued by the New Zealand Patent Office in connection with New Zealand Application No. 722439.
Aug. 9, 2017 Further Examination Report issued by the New Zealand Patent Office in connection with New Zealand Patent Application No. 722439.
Nov. 9, 2017 Response to Aug. 9, 2017 Further Examination Report issued by the New Zealand Patent Office in connection with New Zealand Patent Application No. 722439.
Nov. 20, 2017 Further Examination Report issued by the New Zealand Patent Office in connection with New Zealand Patent Application No. 722439.
Dec. 12, 2017 Response to Nov. 20, 2017 Further Examination Report issued by the New Zealand Patent Office in connection with New Zealand Patent Application No. 722439.
Apr. 10, 2017 Office Action issued by the Panamanian Patent Office in connection with Panamanian Patent Application No. 91211 (including English language translation).
Dec. 22, 2017 Response to Apr. 10, 2017 Office Action issued by the Panamanian Patent Office in connection with Panamanian Patent Application No. 91211.
Jul. 24, 2017 Technical Examination Report issued by the Salvadorian Patent Office in connection with Salvadorian Patent Application No. 20160020316 (including English language translation).
Nov. 23, 2017 Response to Jul. 24, 2017 Technical Examination Report issued by the Salvadorian Patent Office in connection with Salvadorian Patent Application No. 20160020316.
Dec. 12, 2017 Technical Examination Report issued by the Salvadorian Patent Office in connection with Salvadorian Patent Application No. 20160020316 (including English language translation).
Oct. 5, 2016 Communication pursuant to Rules 161(2) and 162 issued by the European Patent Office in connection with European Patent Application No. 14875976.4.
Jun. 13, 2017 Communication pursuant to Rule 164(1) EPC and Partial Supplementary European Search Report issued by the European Patent Office in connection with European Patent Application No. 14875976.4.
Sep. 15, 2017 European Supplementary Search Report issued by the European Patent Office in connection with European Patent Application No. 14875976.4.
Oct. 4, 2017 Communication pursuant to Rules 70(2) and 70a(2) issued by the European Patent Office in connection with European Patent Application No. 14875976.4.
Apr. 13, 2018 Response to Sep. 15, 2017 European Supplementary Search Report issued by the European Patent Office in connection with European Patent Application No. 14875976.4.
Jun. 14, 2017 Office Action issued by the Eurasian Patent Office in connection with Eurasian Patent Application No. 201691351 (including English language translation).
Oct. 16, 2017 Response to Jun. 14, 2017 Office Action issued by the Eurasian Patent Office in connection with Eurasian Patent Application No. 201691351.
Jan. 26, 2018 Office Action issued by the Eurasian Patent Office in connection with Eurasian Patent Application No. 201691351 (including English language translation).
Dec. 23, 2016 First Examination Report issued by the Australian Patent Office in connection with Australian Patent Application No. 2014373961.
Sep. 27, 2017 Response to Dec. 23, 2016 First Examination Report issued by the Australian Patent Office in connection with Australian Patent Application No. 2014373961.
Nov. 20, 2016 Response to Jul. 20, 2016 Notice Before Examination issued by the Israeli Patent Office in connection with Israeli Patent Application No. 246512.
Jan. 12, 2017 First Examination Report issued by the New Zealand Patent Office in connection with New Zealand Patent Application No. 722438.
Jul. 12, 2017 Response to Jan. 12, 2017 First Examination Report issued by the New Zealand Patent Office in connection with New Zealand Patent Application No. 722438.
Aug. 9, 2017 Further Examination Report issued by the New Zealand Patent Office in connection with New Zealand Patent Application No. 722438.

(56) References Cited

OTHER PUBLICATIONS

May 15, 2020 Summons to attend Oral Proceedings pursuant to Rule 115(1) EPC issued by the European Patent Office in connection with European Patent Application No. 14877285.8.

Oct. 2, 2020 Written Submissions to May 15, 2020 Summons to attend Oral Proceedings pursuant to Rule 115(1) EPC issued by the European Patent Office in connection with European Patent Application No. 14877285.8.

Jul. 13, 2020 Response to Apr. 3, 2020 Office Action issued by the Brazilian Patent Office in connection with Brazilian Patent Application No. BR 102014033010-0.

Sep. 14, 2020 Office Action issued by the Brazilian Patent Office in connection with Brazilian Patent Application No. BR 102014033010-0.

Jul. 21, 2020 Response to Jan. 21, 2020 Office Action issued by the Japanese Patent Office in connection with Japanese Patent Application No. 2016-543746.

Jul. 6, 2020 Response to Feb. 6, 2020 Office Action issued by the Mexican Patent Office in connection with Mexican Patent Application No. MX/a/2016/008758.

May 15, 2020 Summons to attend Oral Proceedings pursuant to Rule 115(1) EPC issued by the European Patent Office in connection with European Patent Application No. 14875976.4.

Oct. 2, 2020 Written Submissions to May 15, 2020 Summons to attend Oral Proceedings pursuant to Rule 115(1) EPC issued by the European Patent Office in connection with European Patent Application No. 14875976.4.

Jul. 21, 2020 Response to Apr. 15, 2020 Office Action issued by the Brazilian Patent Office in connection with Brazilian Patent Application No. BR 102014033037-2.

Jul. 29, 2020 Response to Jul. 29, 2020 Office Action issued by the Brazilian Patent Office in connection with Brazilian Patent Application No. BR 102014033037-2.

Sep. 14, 2020 Office Action issued by the Brazilian Patent Office in connection with Brazilian Patent Application No. BR 102014033037-2.

Jul. 7, 2020 Response to Dec. 16, 2019 Office Action issued by the Mexican Patent Office in connection with Mexican Patent Application No. MX/a/2016/008759.

5-FLUORO-4-IMINO-3(ALKYL/SUBSTITUTED ALKYL)-1-(ARYLSULFONYL)-3,4-DIHYDROPYRIMIDIN-2(1H)-ONE AND PROCESSES FOR THEIR PREPARATION

CROSS REFERENCE TO RELATED APPLICATIONS

This application is a continuation of U.S. Ser. No. 16/585,239, filed Sep. 27, 2019, which is a continuation of U.S. Ser. No. 16/448,633, filed Jun. 21, 2019, which is a continuation of U.S. Ser. No. 15/813,562, filed Nov. 15, 2017, now abandoned, which is a continuation of U.S. Ser. No. 15/173,493, filed Jun. 3, 2016, now U.S. Pat. No. 9,850,215, issued Dec. 26, 2017, which is a continuation of U.S. Ser. No. 14/584,347, filed Dec. 29, 2014, now abandoned, which claims the benefit of U.S. Provisional Patent Application Ser. Nos. 61/922,582 and 61/922,572, each filed Dec. 31, 2013, the disclosures of each are expressly incorporated by reference herein.

FIELD

Provided herein are 5-fluoro-4-imino-3-(alkyl/substituted alkyl)-1-(arylsulfonyl)-3,4-dihydropyrimidin-2(1H)-one and processes for their preparation.

BACKGROUND AND SUMMARY

U.S. patent application Ser. No. 13/090,616, U.S. Pub. No. 2011/0263627, describes inter alia certain N3-substituted-N1-sulfonyl-5-fluoropyrimidinone compounds and their use as fungicides. The disclosure of the application is expressly incorporated by reference herein. This patent describes various routes to generate N3-substituted-N1-sulfonyl-5-fluoropyrimidinone compounds. It may be advantageous to provide more direct and efficient methods for the preparation, isolation, and purification of N3-substituted-N1-sulfonyl-5-fluoropyrimidinone fungicides and related compounds, e.g., by the use of reagents and/or chemical intermediates and isolation and purification techniques which provide improved time and cost efficiency.

Provided herein are 5-fluoro-4-imino-3-(alkyl/substituted alkyl)-1-(arylsulfonyl)-3,4-dihydropyrimidin-2(1H)-one and processes for their preparation. In one embodiment, provided herein is a process for the preparation of compounds of Formula III:

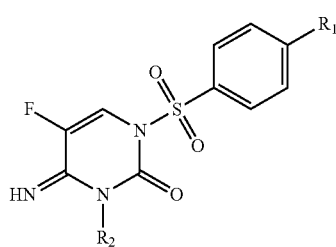

Wherein $R_1$ is selected from:

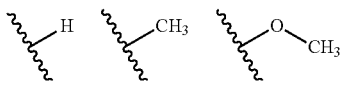

and $R_2$ is selected from:

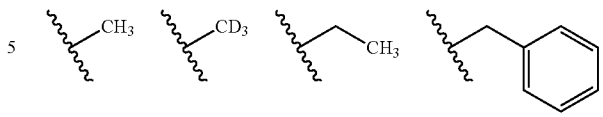

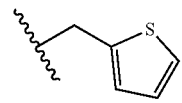

which comprises contacting compounds of Formula II with a base, such as an alkali carbonate, e.g., sodium-, potassium-, cesium-, and lithium carbonate ($Na_2CO_3$, $K_2CO_3$, $Cs_2CO_3$, and $Li_2CO_3$, respectively) or an alkali alkoxide, for example, potassium tert-butoxide ($KO^tBu$) and an alkylating agent, such as an alkyl halide of Formula $R_2$—X, wherein $R_2$ is as previously defined and X is a halogen, e.g., iodine, bromine, and chlorine, in a polar solvent, such as N,N-dimethylformamide (DMF), dimethylsulfoxide (DMSO), dimethylacetamide (DMA), N-methylpyrrolidone (NMP), acetonitrile ($CH_3CN$), and the like, at concentrations from about 0.1 molar (M) to about 3 M. In some embodiments, a molar ratio of compounds of Formula II to the base is from about 3:1 to about 1:1 and a molar ratio of compounds of Formula II to alkylating agent is from about 1:1 to about 3:1. In other embodiments, molar ratios of compounds of Formula H to the base and compounds of Formula II to the alkylating agent of about 2:1 and 1:3, respectively, are used. In some embodiments, the reactions are conducted at temperatures between −78° C. and 90° C., and in other embodiments, the reactions are conducted between 22° C. and 60° C.

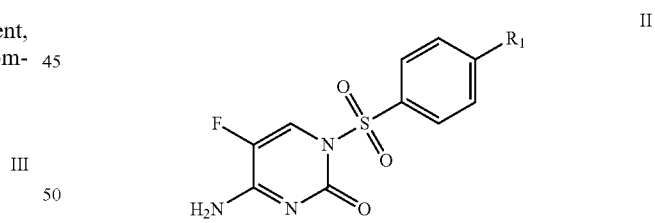

It will be understood by those skilled in the art that manipulation of the reaction parameters described above may result in the formation of product mixtures comprised of compounds of Formulas II, III, and IV, as shown in Scheme 1, wherein the ratios of compounds of Formulas II, III, and IV formed is from about 0:2:1 to about 1:2:0. In some embodiments, compositions comprising mixtures of compounds of Formulas II and III are preferred, as isolation and purification can be achieved through precipitation and recrystallization, and the intermediate compounds of Formula II can be recovered and recycled. In contrast, compositions comprising mixtures of compounds of Formulas III and IV require chromatographic separation to give III along with the undesired dialkylated by-product of Formula IV.

Scheme 1.

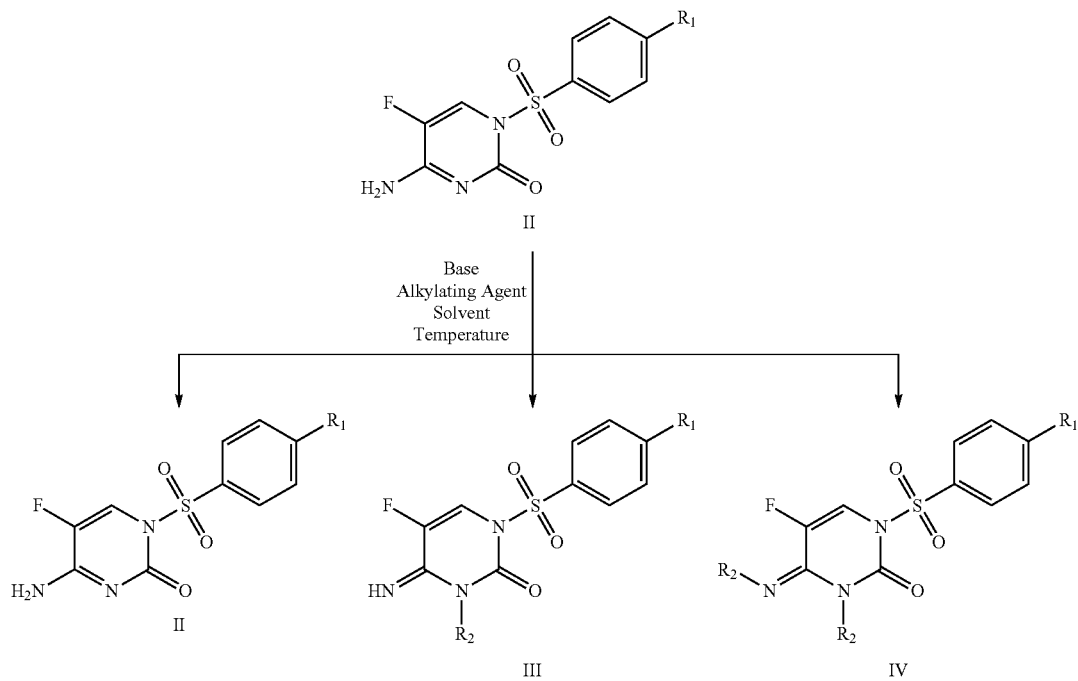

In another embodiment, the desired crude composition, i.e., mixtures of compounds of Formula II and compounds of Formula III, wherein $R_1$ is methoxy ($OCH_3$) and $R_2$ is methyl ($CH_3$), is obtained through contacting a compound of Formula II with $Li_2CO_3$ and methyl iodide ($CH_3I$) in DMF (1.0 M) in a molar ratio of about 1:0.6:3 at 45° C. Upon completion, dilution of the crude composition with a polar, aprotic solvent, such as $CH_3CN$, wherein the ratio of $CH_3CN$:DMF is from about 2:1 to about 1:2, followed by an aqueous solution of sodium thiosulfate ($Na_2S_2O_3$) with a pH from about 8 to about 10.5, wherein the ratio of 2.5 wt. % aqueous $Na_2S_2O_3$:DMF is from about 1:2 to about 3:1, affords a precipitate which is isolable by filtration. In one embodiment, the ratio of $CH_3CN$:DMF is about 1:2 and the ratio of 2.5% aqueous $Na_2S_2O_3$:DMF is about 1:1, and the resultant solid is further purified by crystallization/precipitation from a warmed solution, about 30° C.-40° C., of the solid in a solution of a polar, aprotic solvent, such as $CH_3CN$, by the addition of water ($H_2O$), wherein the ratio of $H_2O$:$CH_3CN$ is from about 1:2 to about 3:1, to give the purified compound of Formula III, and in another embodiment the ratio of $H_2O$:$CH_3CN$ to affect precipitation of pure III is about 2:1.

In another embodiment, compounds of Formula II may be prepared by contacting compounds of Formula I with bis-N,O-trimethylsilylacetamide (BSA) at an elevated temperature, such as 70° C., for a period of about 1 hour (h), followed by cooling and contacting the solution containing the protected pyrimidinol with a substituted benzene sulfonyl chloride, generalized by $R_1$-$PhSO_2Cl$, wherein $R_1$ is as previously defined, at about 20° C.-25° C. In some embodiments, the molar ratio of the compound of Formula I to BSA and the sulfonyl chloride is about 1:3:1.1, respectively, and in another embodiment reducing the molar ratio of the reactants to about 1:1.1:1.1 affords improved yields.

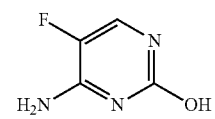

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "aryl" refers to any aromatic, mono- or bi-cyclic, containing heteroatoms.

The term "heterocycle" refers to any aromatic or non-aromatic ring, mono- or bi-cyclic, containing one or more heteroatoms.

The term "alkoxy" refers to an —OR substituent

The term "halogen" or "halo" refers to one or more halogen atoms, defined as F, Cl, Br, and I.

The term "haloalkyl" refers to an alkyl, which is substituted with Cl, F, I, or Br or any combination thereof.

Throughout the disclosure, references to the compounds of Formulas I, II, III, and IV are read as also including optical isomers and salts. Exemplary salts may include: hydrochloride, hydrobromide, hydroiodide, and the like. Additionally, the compounds of Formulas I, II, III, and IV may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

In one exemplary embodiment, a method of making a compound of Formula III is provided. The method includes contacting a compound of Formula II with an alkali carbonate and an alkylating agent; and forming a compound of Formula III,

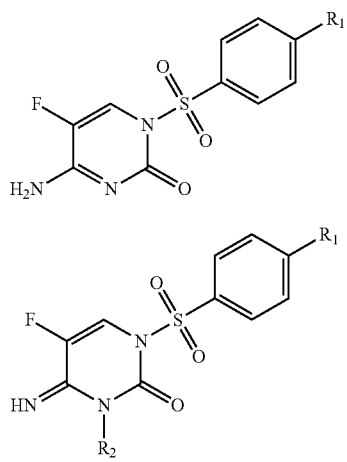

wherein $R_1$ is selected from the group consisting of:

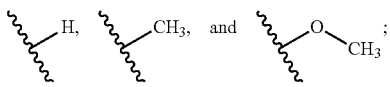

and $R_2$ is selected from the group consisting of:

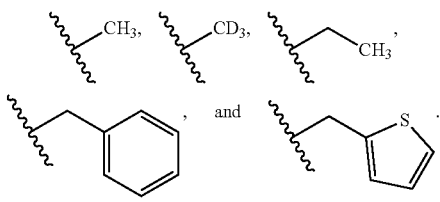

In a more particular embodiment, the contacting step is carried out between 22° C. and 60° C.

In another more particular embodiment of any of the above embodiments, the contacting step further includes a solvent selected from the group consisting of DMF, DMSO, DMA, NMP, and $CH_3CN$.

In another more particular embodiment of any of the above embodiments, the alkali carbonate is selected from the group consisting of: $Na_2CO_3$, $K_2CO_3$, $Cs_2CO_3$, and $Li_2CO_3$.

In another more particular embodiment of any of the above embodiments, the alkylating agent is selected from the group consisting of: alkyl halides and benzyl halides. In an even more particular embodiment, the alkyl halide and benzyl halide are selected from methyl iodide ($CH_3I$) ethyl iodide ($C_2H_5I$), and benzyl bromide (BnBr).

In another more particular embodiment of any of the above embodiments, the alkali carbonate base is $Cs_2CO_3$, and the solvent is DMF.

In another more particular embodiment of any of the above embodiments, a molar ratio of Compound II to alkali carbonate base is from about 3:1 to about 1:1 and a molar ratio of Compound II to alkylating agent is from about 1:1 to about 3:1. In an even more particular embodiment, a molar ratio of Compound II to alkali carbonate base is about 2:1 a molar ratio of Compound II to alkylating agent is 1:3.

In another more particular embodiment of any of the above embodiments, the method further includes the step of diluting a completed reaction mixture with $CH_3CN$ and 2.5% aqueous $Na_2S_2O_3$. In an even more particular embodiment, a ratio of DMF to $CH_3CN$ is from about 1:1 to about 3:1 and a ratio of DMF to 2.5% aqueous $Na_2S_2O_3$ is from about 1:2 to about 2:1. In a still more particular embodiment, a ratio of DMF to $CH_3CN$ is about 2:1 and a ratio of DMF to 2.5% aqueous $Na_2S_2O_3$ is about 1:1.

In another embodiment, a method of preparing a compound of Formula II is provided. The method includes contacting a compound of Formula I with bis-N,O-trimethylsilylacetamide (BSA):

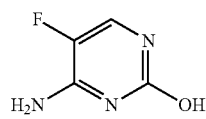

and forming a compound of Formula II:

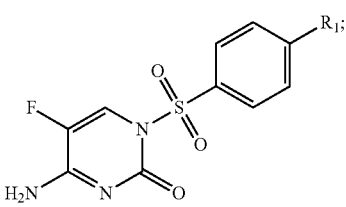

wherein a molar ratio of compound I to bis-N,O-trimethylsilylacetamide (BSA) is 1:1.1 and the contacting step is carried out at about 22° C. to about 70° C.

In a more particular embodiment, the contacting step further includes contacting compound I with $CH_3CN$.

In another more particular embodiment of any of the above embodiments, the method comprises contacting a BSA treated reaction mixture with an arylsulfonyl chloride.

In another more particular embodiment of any of the above embodiments, a molar ratio of Compound I to arylsulfonyl chloride is from about 1:2 to about 2:1. In an even more particular embodiment, a molar ratio of Compound I to arylsulfonyl chloride is 1:1.1.

Another embodiment of the present disclosure may include a fungicidal composition for the control or prevention of fungal attack comprising the compounds described above and a photologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, an area adjacent to the plant, and the seed adapted to produce the plant.

The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

DETAILED DESCRIPTION

5-Fluoro-4-imino-3-(alkyl/substituted alkyl)-1-(arylsulfonyl)-3,4-dihydro-pyrimidin-2(1H)-one as shown in Examples 1-2.

Example 1: Preparation of 4-amino-5-fluoro-1-(phenylsulfonyl)pyrimidin-2(1H)-one (1)

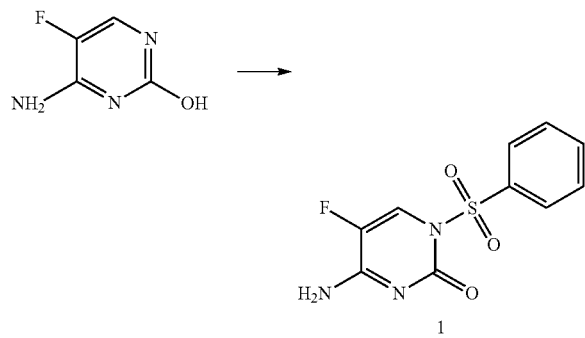

To a dry 500 milliliter (mL) round bottom flask equipped with a mechanical stirrer, nitrogen inlet, addition funnel, thermometer, and reflux condenser were added 5-fluorocytocine (20.0 grams (g), 155 millimole (mmol)) and $CH_3CN$ (100 mL). To the resulting mixture was added BSA (34.7 g, 170 mmol) in one portion and the reaction was warmed to 70° C. and stirred for 30 minutes (min). The resulting homogeneous solution was cooled to 5° C. with an ice bath and treated dropwise with benzenesulfonyl chloride. The reaction was stirred at 0° C.-5° C. for 1 h and then overnight at room temperature. The resulting pale yellow suspension was poured into cold $H_2O$ (1.5 liters (L)) and stirred vigorously for 1 h. The resulting solid was collected by vacuum filtration, washed with $H_2O$, and dried under vacuum overnight at 40° C. to give 4-amino-5-fluoro-1-(phenylsulfonyl)pyrimidin-2(1H)-one (29.9 g, 72%) as a powdery white solid: $^1$H NMR (400 MHz, DMSO-$d_6$) δ 8.56 (s, 1H), 8.35-8.26 (m, 2H), 8.0-7.98 (m, 2H). 7.84-7.74 (m, 1H), 7.72-7.61 (m, 2H); $^{19}$F NMR (376 MHz, DMSO-$d_6$) δ-163.46: ESIMS m/z 270 ([M+H]$^+$).

The following compounds 1-3 in Table 1a were made in accordance with the reaction depicted in Scheme 1 and the procedures described in Example 1. Characterization data for compounds 1-3 are shown in Table 1b.

Scheme 1.

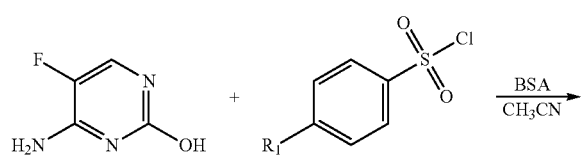

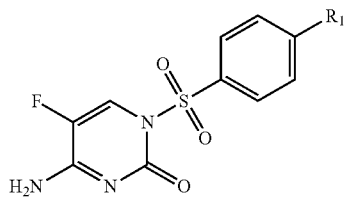

TABLE 1a

| Compound Number | $R_1$ | Appearance | Yield (%) |
|---|---|---|---|
| 1 | H | Powdery White Solid | 72 |
| 2 | $CH_3$ | Powdery White Solid | 61 |
| 3 | $OCH_3$ | Powdery White Solid | 57 |

TABLE 1b

| Compound Number | Mass Spec. | $^1$H NMR (δ)$^a$ | $^{13}$C NMR or $^{19}$F NMR (δ)$^{b,c}$ |
|---|---|---|---|
| 1 | ESIMS m/z 270 ([M + H]$^+$) | $^1$H NMR (DMSO-$d_6$) δ 8.56 (s, 1H), 8.35-8.26 (m, 2H), 8.07-7.98 (m, 2H), 7.84-7.74 (m, 1H), 7.72-7.61 (m, 2H) | $^{19}$F NMR (DMSO-$d_6$) δ - 163.46 |
| 2 | ESIMS m/z 284 ([M + H]$^+$) | $^1$H NMR (DMSO-$d_6$) δ 8.54 (s, 1H), 8.40-8.16 (m, 2H), 8.05-7.76 (m, 2H), 7.66-7.36 (m, 2H), 2.41 (s, 3H) | $^{19}$F NMR (DMSO-$d_6$) δ - 163.62 |
| 3 | ESIMS m/z 300 ([M + H]$^+$) | $^1$H NMR (CDCl$_3$) δ 8.10-7.91 (m, 2H), 7.73 (d, J = 5.4 Hz, 2H), 7.11-6.94 (m, 2H), 3.90 (s, 3H), 3.32 (d, J = 0.6 Hz, 3H) | $^{19}$F NMR (CDCl$_3$) δ - 158.58 |

$^a$All $^1$H NMR data measured at 400 MHz unless otherwise noted.
$^b$All $^{13}$C NMR data measured at 101 MHz unless otherwise noted.
$^c$All $^{19}$F NMR data measured at 376 MHz unless otherwise noted.

Example 2: Preparation of 5-fluoro-4-imino-3-methyl-1-tosyl-3,4-dihydropyrimidin-2(1H)-one (5)

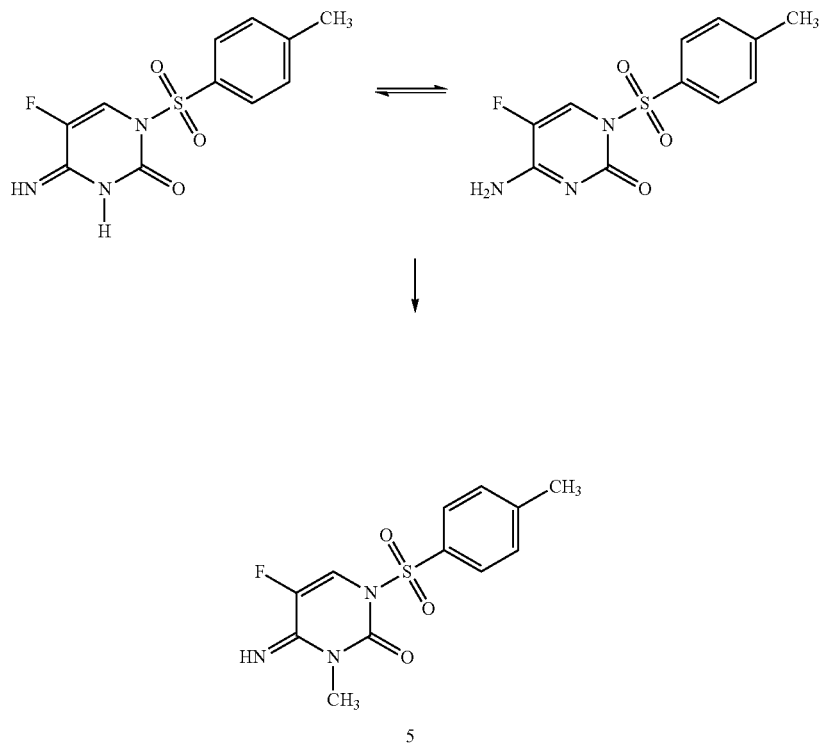

5

To a mixture of 4-amino-5-fluoro-1-tosylpyrimidin-2(1H)-one (5.66 g, 20 mmol) and $Li_2CO_3$ (0.880 g, 12.0 mmol) in DMF (20 mL) was added $CH_3I$ (8.52 g, 60.0 mmol), and the resulting mixture was warmed to 40° C. and stirred for 5 h. The reaction mixture was cooled to room temperature, diluted with $CH_3CN$ (10 ml), and treated with 2.5% aqueous $Na_2S_2O_3$ (20 mL). The resulting mixture was stirred at room temperature for 10 min and the solids were collected b filtration. The filter cake was washed with aqueous $CH_3CN$ (10% $CH_3CN$ in $H_2O$) and air dried for 2 h. The cake was dissolved in $CH_3CN$ (15 mL) at 40° C. and the solution was treated with $H_2O$ (30 mL). The resulting suspension was cooled to room temperature, stirred for 2.5 h, and filtered. The filter cake was again washed with 10% aqueous $CH_3CN$ and then dried under vacuum at 50° C. to give the title compound (2.70 g, 45%) as a white solid: mp 156-158° C.; $^1H$ NMR (400 MHz, DMSO-$d_6$) δ 8.54 (d, J=2.3 Hz, 1H), 7.99 (dd, J=6.0, 0.6 Hz, 1H), 7.95-7.89 (m, 2H), 7.53-7.45 (m, 2H), 3.12 (d, J=0.7 Hz, 3H), 2.42 (s, 3H); $^{19}F$ NMR (376 MHz, DMSO-$d_6$) −157.86 (s); ESIMS m/z 298 ([M+H]$^+$).

The following compounds 4-6 in Table 2a were made in accordance with the reaction depicted in Scheme 2 and the procedures described in Example 2. Characterization data for compounds 4-6 are shown in Table 2b.

Scheme 2.

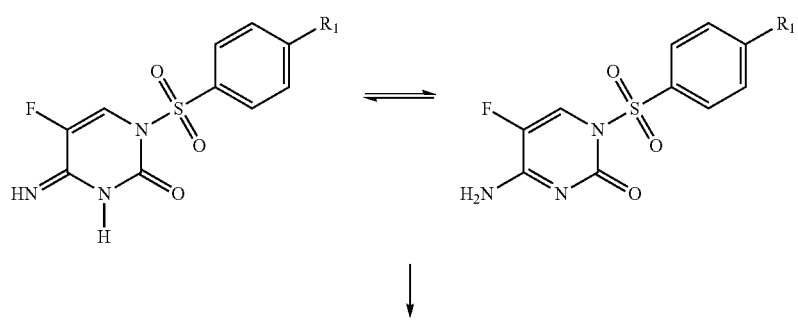

-continued

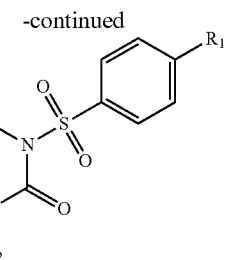

5

TABLE 2a

| Compound Number | R₁ | R₂ | Appearance | Yield (%) |
|---|---|---|---|---|
| 4 | H | CH₃ | White Solid | 64 |
| 5 | CH₃ | CH₃ | White Solid | 45 |
| 6 | OCH₃ | CH₃ | White Solid | 62 |

TABLE 2b

| Compound Number | Mass Spec. | $^1$H NMR (δ)$^a$ | $^{13}$C NMR or $^{19}$F NMR (δ)$^{b,c}$ |
|---|---|---|---|
| 4 | ESIMS m/z 284 ([M + H]⁺) | $^1$H NMR (CDCl₃) δ 8.14-8.02 (m, 2H), 7.88-7.67 (m, 3H), 7.67-7.50 (m, 2H), 3.31 (d, J = 0.7 Hz, 3H) | $^{19}$F NMR (CDCl₃) δ - 158.05 |
| 5 | ESIMS m/z 298 ([M + H]⁺) | $^1$H NMR (DMSO-d₆) δ 8.54 (d, J = 2.3 Hz, 1H), 7.99 (dd, J = 6.0, 0.6 Hz, 1H), 7.95-7.89 (m, 2H), 7.53-7.45 (m, 2H), 3.12 (d, J = 0.7 Hz, 3H), 2.42 (s, 3H) | $^{19}$F NMR (DMSO-d₆) δ 157.86 (s) |
| 6 | ESIMS m/z 314 ([M + H]⁺) | $^1$H NMR (CDCl₃) δ 8.10-7.91 (m, 2H), 7.73 (d, J = 5.4 Hz, 2H), 7.11-6.94 (m, 2H), 3.90 (s, 3H), 3.32 (d, J = 0.6 Hz, 3H) | $^{19}$F NMR (CDCl₃) δ - 158.58 |

$^a$All $^1$H NMR data measured at 400 MHz unless otherwise noted.
$^b$All $^{13}$C NMR data measured at 101 MHz unless otherwise noted.
$^c$All $^{19}$F NMR data measured at 376 MHz unless otherwise noted.

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

Preferably, the compounds of the present disclosure are applied in the form of a formulation comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendible, or emulsifiable formulations which are usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; C₉-C₁₁ alkylpolyglycoside; phosphated alcohol ethoxylate; natural primary alcohol (C₁₂-C₁₆) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungicidal pathogens. Exemplary pathogens may include, but are not limited to, wheat leaf blotch (*Septoria tritici*, also known as *Mycosphaerella graminicola*) apple scab (*Venturia inaequalis*), and *Cercospora* leaf spots of sugar beets (*Cercospora beticola*), peanuts (*Cercospora arachidicola* and *Cercosporidium personatum*) and other crops, and black sigatoka of bananas (*Mycosphaerella fujiensis*). The exact amount of the active material to be applied is dependent not only on the specific active material being applied, but also on the particular action desired, the fungal species to be controlled, and the stage of growth thereof as well as the part of the plant or other product to be contacted with the compound. Thus, all the compounds, and formulations containing the same, may not be equally effective at similar concentrations or against the same fungal species.

What is claimed is:

1. A compound of Formula III:

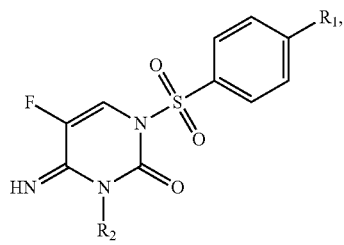

III wherein $R_1$ is

and
$R_2$ is selected from the group consisting of

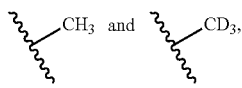

or a tautomer, an optical isomer, or a salt thereof.

2. The compound of claim 1 in the form of a salt.
3. The compound of claim 2, wherein the salt is a hydrochloride, hydrobromide or hydroiodide.
4. The compound of claim 1, wherein $R_2$ is

5. The compound of claim 4 in the form of a salt.
6. The compound of claim 5, wherein the salt is a hydrochloride, hydrobromide or hydroiodide.

7. The compound of claim 1, wherein $R_2$ is

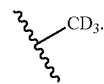

8. The compound of claim 7 in the form of a salt.
9. A method for control or prevention of fungal attack on a plant comprising applying a fungicidally effective amount of a compound of Formula III:

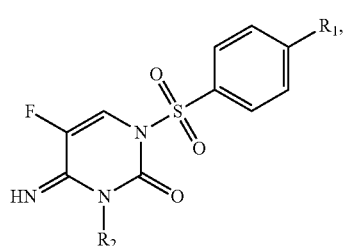

III to at least one of the plant, an area adjacent to the plant, soil adapted to support growth of the plant, a root of the plant, foliage of the plant, and a seed adapted to produce the plant so as to thereby control or prevent fungal attack on the plant, wherein $R_1$ is

and
$R_2$ is selected from the group consisting of

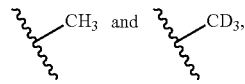

or a tautomer, an optical isomer, or a salt thereof.

10. The method of claim 9, wherein the fungal pathogen is Apple Scab (*Venturia inaequalis*), Leaf Blotch of Wheat (*Septoria tritici*), Leaf spot of sugarbeets (*Cercospora beticola*), Leaf Spot of peanut (*Cercospora arachidicola*), or Black Sigatoka (*Mycosphaerella fijiensis*).

11. The method of claim 9, wherein $R_2$ is

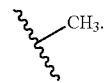

12. The method of claim 11, wherein the compound is in the form of a salt.
13. The method of claim 12, wherein the salt is a hydrochloride, hydrobromide or hydroiodide.

14. The method of claim 9, wherein $R_2$ is

15. The method of claim 9, wherein the method further comprises applying an adjuvant surfactant.

16. The method of claim 15, wherein the adjuvant surfactant is selected from the group consisting of: ethoxylated nonyl phenols; ethoxylated synthetic or natural alcohols; salts of the esters or sulphosuccinic acids; ethoxylated organosilicones; ethoxylated fatty amines; blends of surfactants with mineral or vegetable oils; crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); and PEG(400) dioleate-99.

17. A fungicidal composition comprising a compound of Formula III:

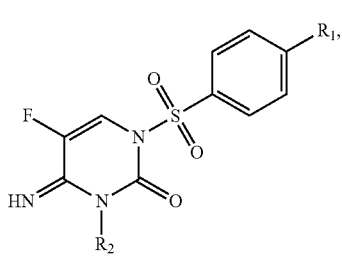

wherein $R_1$ is

and $R_2$ is selected from the group consisting of

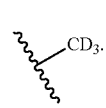

or a tautomer, an optical isomer, or a salt thereof, and a phytologically acceptable carrier material.

18. The composition of claim 17, wherein $R_2$ is $\begin{array}{c}\text{CH}_3.\end{array}$ 19. The composition of claim 17, wherein $R_2$ is $\begin{array}{c}\text{CD}_3.\end{array}$ 20. The composition of claim 17, wherein the composition further comprises an adjuvant surfactant.

* * * * *